(12) United States Patent
Rucker

(10) Patent No.: US 6,960,348 B2
(45) Date of Patent: Nov. 1, 2005

(54) GOYA DERIVED COSMETIC COMPOSITIONS FOR FACE AND BODY

(76) Inventor: Mieko Arashiro Rucker, 451 Sassafras La., Ruckersville, VA (US) 22968

( * ) Notice: Subject to any disclaimer, the term of this patent is extended or adjusted under 35 U.S.C. 154(b) by 585 days.

(21) Appl. No.: 10/236,710

(22) Filed: Sep. 7, 2002

(65) Prior Publication Data

US 2003/0049225 A1 Mar. 13, 2003

Related U.S. Application Data

(60) Provisional application No. 60/318,236, filed on Sep. 10, 2001.

(51) Int. Cl.$^7$ .......................... A61K 6/00; A61K 7/00; A61K 9/00; A61K 35/78
(52) U.S. Cl. ...................... 424/401; 424/400; 424/725
(58) Field of Search ................................ 424/401, 400, 424/725

(56) References Cited

U.S. PATENT DOCUMENTS 5,484,889 A * 1/1996 Lee-Huang et al.
5,851,531 A * 12/1998 Lazarus
6,379,718 B2 * 4/2002 Ren

* cited by examiner

Primary Examiner—Thurman K. Page
Assistant Examiner—Humera N. Sheikh

(57) ABSTRACT

A novel cosmetic preparation can be obtained by incorporating goya (*momordica charantia*) fruit and leaves into generic paraffin and cosmetic clay. The unique result can be used by estheticians in providing facial masks and cosmetic skin applications in beauty salons or spas and by individuals for similar cosmetic purposes at home.

3 Claims, No Drawings

GOYA DERIVED COSMETIC COMPOSITIONS FOR FACE AND BODY

This application claims the benefit of provisional application No. 60/318,236 filed Sep. 10, 2001.

CROSS-REFERENCE TO RELATED APPLICATIONS

Not Applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not Applicable.

BACKGROUND OF THE INVENTION

This invention involves the discovery that *momordica charantia* can be incorporated into generic cosmetic wax or clay to increase its effectiveness both functionally and aesthetically.

This invention pertains to:

Class 424, Drug, Bio-Affecting and Body Treating Compositions. (B) Body Treating Compositions generally intended for deodorizing, protecting, adorning, or grooming a body; e.g., cosmetics, dentifrices, embalming fluids, etc. Subclass 725, Plant Material or Plant Extract of Undetermined Constitution as Active Ingredient (e.g., herbal remedy, herbal extracts, powder, oil, etc.)

*Momordica charantia* is commonly cultivated in Africa and Asia, and the immature fruit and leaves have long been used in Asian cooking. The fruit and leaves also have long been used as folk-medicine remedies for a variety of ills.

The immature fruit (which is used in this invention) is a good source of Vitamin C and also contains Vitamin A, phosphorus, and iron. The tender leaves (which also are used in this invention) are an excellent source of vitamin A and contain protein, thiamin, and Vitamin C. Recent investigation suggests that *mormordica charantia* has potential medicinal value in treating certain immunodeficiencies, diabetes, and acne or furuncles.

The *mormordica charantia* plant is a climbing vine. In appearance, the fruit resembles a "bumpy" cucumber. The fruit and plant are known in different cultures by many names, a few of which are bitter melon, African cucumber, karela, mara, muop dang, niga-uri, and ampalaya. In this invention, goya, the Okinawan name for momordica charantia, is used.

Goya is grown commercially in the United States, chiefly for use in Oriental cooking. Extracts are available through herbal outlets and are offered as nutritional supplements. A process for incorporating any form of goya in facial masks and cosmetic skin care, however, is unique.

One major service an esthetician provides clients is application of paraffin wax or cosmetic mud to the client's body, especially to the face. With removal of the wax or clay, the client feels the skin is softer, smoother, and refreshed.

Estheticians frequently add ingredients to generic paraffin wax or cosmetic clay in order to increase the emollient or aromatic efficacy. Also, the client should perceive additives to the paraffin wax or clay as cosmetically elegant or exotic. The uniqueness of this invention is its incorporation of goya as the leading additive to achieve the above results.

References:

U.S. PATENT DOCUMENTS

U.S. Pat. No. 5,484,889 Plant protein useful for treating tumors and HIV infection U.S. Pat. No. 5,851,531 Adult-onset diabetes treatment method U.S. Pat. No. 6,379,718 Use of plant extracts for treatment of acne and furuncle

OTHER

Internet searches under "*mormordica charantia*" and "bitter melon" lead to an abundance of websites and information, e.g. horticultural, medical, herbal, taxonomic, academic, USDA, and USPTO.

BRIEF DESCRIPTION OF THE SEVERAL VIEWS OF THE DRAWING

Not Applicable.

DETAILED DESCRIPTION OF THE INVENTION

The uniqueness of this invention results from incorporating goya fruit and leaves into a paraffin wax or clay so that an esthetician may apply it in cosmetic facial masks and cosmetic skin treatments. Depending on the availability of goya fruit and leaves as well as the preferences of the esthetician and client, the process may involve use of goya fruit only, of goya leaves only, or a combination of fruit and leaves.

The process may begin with green, immature goya fruit or with tender green goya leaves. During the cleaning, preparation, and drying steps, the fruit and leaves must be treated differently as described below.

The fruit: Wash thoroughly in cold water. Inspect carefully and remove any foreign matter. Slice in half lengthwise. Scoop out seeds and discard. Chop crosswise into quarter-inch sections. Use dehydrator approximately one day to remove all moisture. (Time required varies according to section size and dehydrator used.)

The leaves: Wash thoroughly in cold water. Inspect carefully and remove any foreign matter. Use dehydrator approximately one day to remove all moisture. Adjust time as required.

The following steps are the same whether processing dried goya fruit or dried goya leaves.

Grind dried goya fruit sections or dried leaves into powder using food processor or similar instrument.

Blend powder (ground from dried fruit, from dried leaves, or from a combination of both) into warm oil, preferably olive oil or sunflower oil, approximately 1 ounce of powder to 1 pint of oil. The resulting goya oil should be stored in a capped glass container until it is to be combined with paraffin or clay for application.

When combining goya oil with generic paraffin and cosmetic clay, the esthetician should insure that all ingredients are warm in order to facilitate smooth and thorough blending. The actual amount of goya oil solution added to the paraffin or clay for facial masks or body wraps may vary depending on the esthetician's or client's preferences.

The esthetician then uses the same steps in applying goya-based paraffin or cosmetic clay to the client as would be used with standard facial masks or body wraps not incorporating goya.

What is claimed is:

1. A cosmetic composition comprising a green, immature goya fruit solution and paraffin, wherein said solution comprises immature goya fruit and an oil selected from the group consisting of olive oil and sunflower oil, in a ratio of 1 ounce of goya powder to 1 pint of oil.

2. A cosmetic composition comprising a green, immature goya fruit solution and clay, wherein said solution comprises immature goya fruit and an oil selected from the group consisting of olive oil and sunflower oil, in a ratio of 1 ounce of goya powder to 1 pint of oil.

3. A method of softening skin using the cosmetic composition of claim 1 or 2 which comprises applying the composition to the face or body.

* * * * *